(12) United States Patent
Pickles et al.

(10) Patent No.: US 10,041,895 B2
(45) Date of Patent: Aug. 7, 2018

(54) SENSING SYSTEM USING A MARGINAL OSCILLATOR

(71) Applicant: Salunda Limited, Oxfordshire (GB)

(72) Inventors: Philip Samuel Pickles, Oxfordshire (GB); Peter Wherritt, Oxfordshire (GB); Martin Roy Harrison, Northants (GB)

(73) Assignee: Salunda Limited, Oxfordshire (GB)

(*) Notice: Subject to any disclaimer, the term of this patent is extended or adjusted under 35 U.S.C. 154(b) by 0 days.

(21) Appl. No.: 14/908,812

(22) PCT Filed: Jun. 19, 2014

(86) PCT No.: PCT/GB2014/051886
§ 371 (c)(1),
(2) Date: Jan. 29, 2016

(87) PCT Pub. No.: WO2015/015150
PCT Pub. Date: Feb. 5, 2015

(65) Prior Publication Data
US 2016/0187275 A1 Jun. 30, 2016

(30) Foreign Application Priority Data
Jul. 31, 2013 (GB) .................................. 1313725.2

(51) Int. Cl.
*G01N 27/02* (2006.01)
*G01N 27/22* (2006.01)
(Continued)

(52) U.S. Cl.
CPC ......... *G01N 27/025* (2013.01); *G01D 5/2405* (2013.01); *G01N 27/228* (2013.01); *G01R 27/26* (2013.01)

(58) Field of Classification Search
CPC .......... G01D 5/14; G01D 5/24; G01D 5/2405; G01N 27/02; G01N 27/023; G01N 27/025;
(Continued)

(56) References Cited

U.S. PATENT DOCUMENTS 4,797,614 A * 1/1989 Nelson ................... G01R 27/02
324/224
4,837,511 A   6/1989 Whittington et al.
(Continued)

FOREIGN PATENT DOCUMENTS

GB         1408862 A      10/1975
WO   WO-0169168 A1    9/2001

*Primary Examiner* — Huy Q Phan
*Assistant Examiner* — David Frederiksen
(74) *Attorney, Agent, or Firm* — Honigman Miller Schwartz and Cohn LLP

(57) ABSTRACT

A sensor system comprises a marginal oscillator. A tank circuit comprises inductive and capacitive elements including a probe arranged to generate an electromagnetic field in a sensing region. A non-linear drive circuit drives oscillation of the tank circuit by supplying a differential signal pair of complementary signals across the tank circuit, sustaining the oscillation on the basis of at least one of the complementary signals. A detection circuit detects a characteristic of the oscillation of the tank circuit that is dependent on the electromagnetic properties of the contents of the sensing region and to derive a signal representing the at least one characteristic. The differential signaling provides numerous advantages, including improved accuracy and signal-to-noise.

16 Claims, 2 Drawing Sheets

(51) Int. Cl.
*G01D 5/24* (2006.01)
*G01R 27/26* (2006.01)

(58) Field of Classification Search
CPC ...... G01N 27/028; G01N 27/04; G01N 27/22;
G01N 27/221; G01N 27/228; A61B 5/05;
A61B 5/053
See application file for complete search history.

(56) References Cited

U.S. PATENT DOCUMENTS

| | | | | |
|---|---|---|---|---|
| 4,975,800 A * | 12/1990 | Oshita | ................ | G01R 31/3274 324/520 |
| 6,072,320 A * | 6/2000 | Verkuil | ................ | G01R 31/311 324/754.23 |
| 2003/0179000 A1* | 9/2003 | Gregg | ................ | G01D 5/2013 324/655 |
| 2004/0034274 A1* | 2/2004 | Brady | ................ | A61B 5/053 600/29 |
| 2004/0113707 A1 | 6/2004 | Fredriksson | | |
| 2007/0108972 A1* | 5/2007 | Blew | ................ | A61B 5/02028 324/239 |
| 2010/0079136 A1* | 4/2010 | Phillips | ................ | F01D 11/20 324/207.16 |
| 2010/0107284 A1* | 4/2010 | Shigeno | ................ | B82Y 35/00 850/5 |
| 2010/0225332 A1* | 9/2010 | Niwa | ................ | H03K 17/9502 324/652 |
| 2010/0231239 A1* | 9/2010 | Tateishi | ................ | G01D 5/24 324/672 |
| 2011/0128014 A1* | 6/2011 | Harrison | ................ | G01D 5/145 324/601 |
| 2011/0267078 A1* | 11/2011 | Eilersen | ................ | G01R 27/2605 324/658 |
| 2012/0326711 A1* | 12/2012 | Roper | ................ | G01N 27/025 324/252 |
| 2013/0176038 A1 | 7/2013 | Wherritt | | |
| 2013/0181718 A1* | 7/2013 | Richardson | ................ | G01V 3/101 324/327 |

* cited by examiner

SENSING SYSTEM USING A MARGINAL OSCILLATOR

The present invention relates to sensing of the electromagnetic properties of the contents of a sensing region using a marginal oscillator.

BACKGROUND

A marginal oscillator is a self-oscillating oscillator that generates oscillations in a tank circuit comprising inductive and capacitive elements at the natural frequency of the tank circuit. Oscillation of the tank circuit is driven by a non-linear drive circuit that sustains the oscillation on the basis of the signal across the tank circuit. The non-linear drive circuit has a non-linear gain so as to achieve a steady-state oscillation.

A marginal oscillator may be used as a sensor system to perform sensing by using elements of the tank circuit as an inductive or capacitive probe that generates an electromagnetic field in a sensing region. A characteristic of the oscillation of the tank circuit that is dependent on the electromagnetic properties of the contents of the sensing region may be detected by a detection circuit to derive a signal representing the characteristic. This, this signal is also representing the electromagnetic properties of the contents of the sensing region.

A type of marginal oscillator is a Robinson marginal oscillator, in which the non-linear drive circuit includes a gain stage that amplifies the signal across the tank circuit supplied back to the non-linear drive circuit and a limiter stage that limits the output of the gain stage for generating a drive signal supplied to the tank circuit. By separating the gain and limiter stages, the signal-to-noise ratio is improved.

Marginal oscillators were originally developed for detection of nuclear magnetic resonance. More recently, they have been used as sensor systems for sensing the electromagnetic properties of the contents of the sensing region, for example an object or a material in the sensing region. By way of example, WO-01/69168 discloses use of a Robinson marginal oscillator in a sensor system for sensing the electric or magnetic susceptibility of an object, for example to detect the position of the object. Marginal oscillators, and Robinson marginal oscillator in particular, provide particular advantages compared to other sensors, for example providing accurate sensing applicable to a wide range of systems to be sensed.

SUMMARY

The present invention is concerned with improving the performance of such a marginal oscillator used as a sensor system for sensing.

According to a first aspect of the present invention, there is provided a sensor system comprising:

a marginal oscillator comprising:

a tank circuit comprising inductive and capacitive elements that include an inductive or capacitive probe arranged to generate an electromagnetic field in a sensing region, and a non-linear drive circuit arranged to drive oscillation of the tank circuit by supplying a differential signal pair of complementary signals across the tank circuit, the non-linear drive circuit being arranged to sustain the oscillation on the basis of at least one of the complementary signals supplied back to the non-linear drive circuit; and a detection circuit arranged to detect at least one characteristic of the oscillation of the tank circuit that is dependent on the electromagnetic properties of the contents of the sensing region and to derive a signal representing the at least one characteristic.

Thus, in the marginal oscillator, which may be a Robinson marginal oscillator, the present invention uses a non-linear drive circuit that supplies a differential signal pair of complementary signals across the tank circuit. A complementary signal is supplied to each end of the tank circuit and the overall signal across the tank circuit is a differential signal, that is the difference between the complementary signals. This makes the oscillator into a differential system rather than just using a single-ended signal with respect to ground. Such differential signaling across the tank circuit can provide numerous advantages, whilst maintaining advantages of using a marginal oscillators, and Robinson marginal oscillator in particular, as a sensing system.

Some examples of the advantages that may be achieved are as follows, although different advantages may be significant in different applications.

One advantage arises from the ground becoming electrically isolated from the rest of the system. This reduces the effects of uncontrolled ground paths associated with the probe which may otherwise introduce error in the sensing by affecting the detected characteristic in an unpredictable manner. By reducing such effects, the accuracy of the sensing may be improved and/or the screening requirements of the probe may be reduced resulting in easier implementation of the probe in respect of the system being sensed. Similarly, the sensor system may have a reduced tendency to pick up external oscillations and an improved signal-to-noise ratio.

An illustrative example of this advantage may be seen in the case that the probe is a capacitive probe that senses the contents of a pipe formed of insulating material, for example comprising a pair of conductive rings arranged around the pipe at positions spaced apart along the pipe. This type of probe forms the sensing region between the rings and therefore provides for sensing of the contents of the pipe in a convenient manner. In this case, although the pipe is formed of insulating material, there are typically associated elements formed of conductive material that may be grounded, for example flanges forming pipe connections, that affect the output signal but not necessarily in a predictable manner. The effect of the differential signaling electrically isolating the ground reduces the impact of uncontrolled ground paths formed by such elements, thereby improving accuracy.

Another advantage occurs in the optional case that the probe is connected to the remainder of the tank circuit by cabling. In that case, the differential signaling reduces the impact of the cabling on the detected signal, thereby improving sensitivity.

Another advantage may be that starting of the marginal oscillator may be improved compared to a single-ended marginal oscillator. Whilst a single-ended marginal oscillator may effectively sustain an oscillation that already exists, starting the oscillation might not happen spontaneously and may require a special arrangement. However, in the differential system of the present invention, oscillation may start more readily.

Advantageously, starting may be improved in particular by arranging the non-linear drive circuit so that the complementary signals have unbalanced amplitudes. If the oscillator is intentionally unbalanced in this way, the differential nature of the signal will ensure starting will always occur.

Another advantage may be that the marginal oscillator has defined fault states observable in the frequency of oscillation to allow detection of faulty operation, which can be difficult in the case of a marginal oscillator employing a single-ended signal. For example, in the case that the probe is an inductive probe, then removal of the probe (open circuit case) will result in the oscillation ceasing and shorting of the probe (closed circuit case) will result in the frequency of oscillation becoming unusually high. Similarly, in the case that the probe is a capacitive probe, then removal or shorting of the probe will result in the frequency of oscillation becoming unusually high. Thus, faults may be detected when the frequency of oscillation is observed to fall outside a predetermined band corresponding to normal operation.

According to a second aspect of the present invention, there is provided a method of sensing electromagnetic properties of the contents of a sensing region, the method using a marginal oscillator comprising:

a tank circuit comprising inductive and capacitive elements that include an inductive or capacitive probe arranged to generate an electromagnetic field in the sensing region, and a non-linear drive circuit arranged to drive oscillation of the tank circuit by supplying a differential signal pair of complementary signals across the tank circuit, the non-linear drive circuit being arranged to sustain the oscillation on the basis of at least one of the complementary signals supplied back to the non-linear drive circuit, the method comprising operating the marginal oscillator to provide oscillation of the tank circuit and detecting at least one characteristic of the oscillation of the tank circuit that is dependent on the electromagnetic properties of the contents of the sensing region.

Thus, the marginal oscillator is made into a differential system in the same manner as the first aspect of the present invention, and so similar advantages are achieved.

The present invention in accordance with both the first and second aspects may be applied to advantage in a wide range of applications. Some non-limitative examples include applications which require long lengths of cabling, such as turbine blade sensing, and include applications for sensing the contents of a pipe formed of insulating material.

Depending on the application, different characteristics of the oscillation of the tank circuit may be detected, for example as follows.

The characteristic of the oscillation of the tank circuit may include the amplitude of the oscillation of the tank circuit. The electromagnetic properties of the contents of the sensing region on which this type of characteristic is dependent on the imaginary part of the electric or magnetic susceptibility, that is the losses or conductivity. This may be used, for example, to sense the conductivity of the contents of the sensing region. In the case of sensing the contents of a pipe containing a mixture of water and hydrocarbons in a water-continuous phase, the sense conductivity may be used in sensing of the salinity.

In this case, the amplitude of the oscillation of the tank circuit may be detected differentially. This is not essential, but further improves the sensitivity.

The characteristic of the oscillation of the tank circuit may include the frequency of the oscillation of the tank circuit. The electromagnetic properties of the contents of the sensing region on which this type of characteristic is dependent are the real part of the electric or magnetic susceptibility.

However, these characteristics are not limitative and any other characteristic may be detected, for example the Q factor.

BRIEF DESCRIPTION OF THE DRAWINGS

Embodiments of the present invention will now be described by way of non-limitative example with reference to the accompanying drawings, in which.

DETAILED DESCRIPTION

Figure 1:
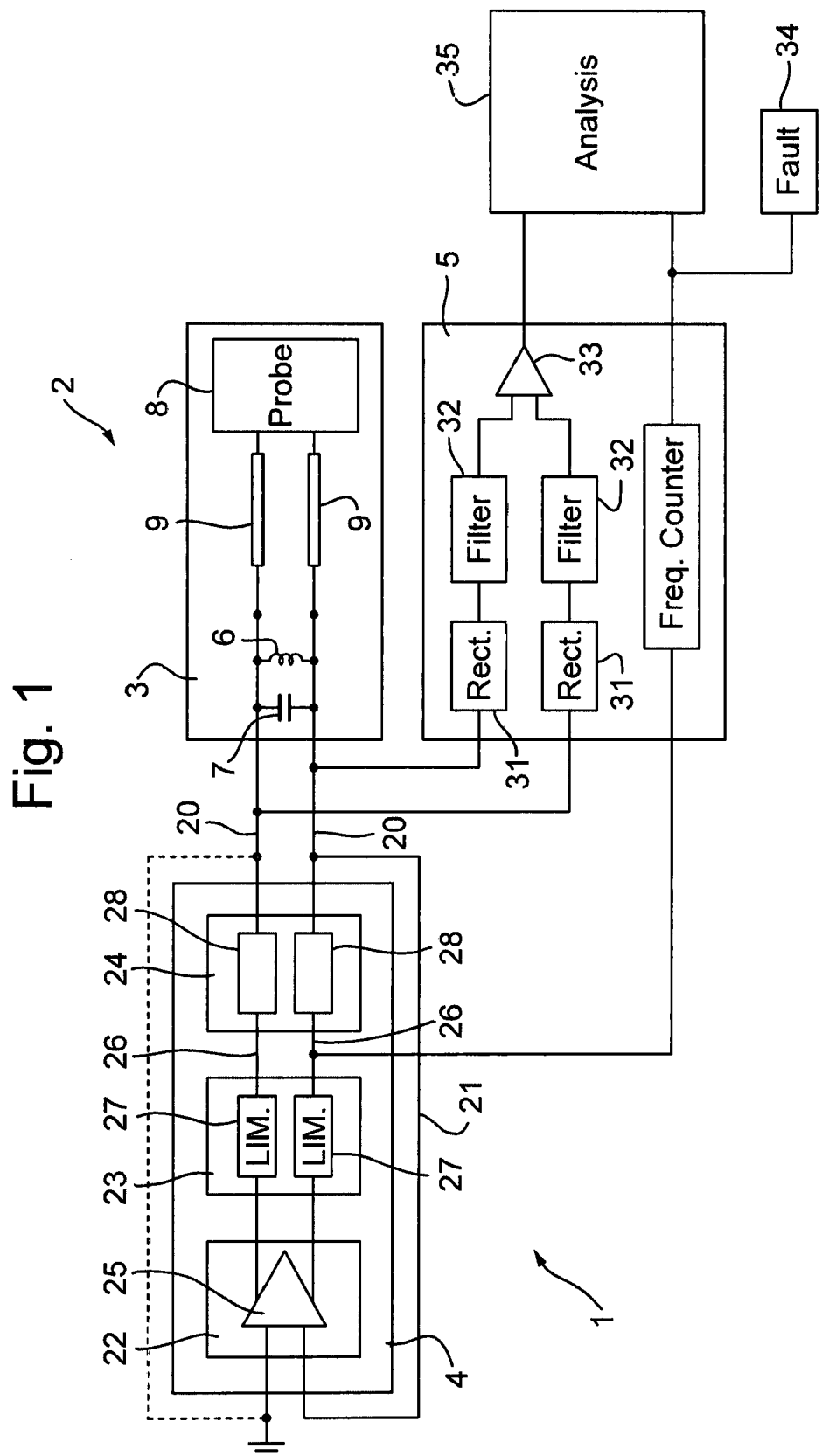
FIG. 1 is a circuit diagram of a sensor system.

A sensor system 1 is shown in FIG. 1 and arranged as follows.

The sensor system 1 includes a marginal oscillator 2 comprising a tank circuit 3 and a non-linear drive circuit 4. The sensor system 1 also includes a detection circuit 5.

The tank circuit 3 is a resonant circuit. In this example the tank circuit 3 comprises an inductor 6, a capacitor 7 and a probe 8 connected in parallel with each other, but in general the tank circuit 3 may include any arrangement of inductive element and capacitive elements, one of which forms a probe.

The probe 8 is connected by cabling 9 to the inductor 5 and capacitor 6 forming the remainder of the tank circuit 3. The cabling 9 may be cables in respect of each connection to the probe 8, which may be coaxial cables. The cabling 9 allows the probe 8 to be located remotely from the remainder of the marginal oscillator 2, although in situations where this is not necessary the sensor system 1 could equally be implemented without the cabling 9.

The differential signaling described below provides particular advantage when the cabling 9 is provided. In that case, with single-ended signaling, the cabling 9 contribute a high capacitance which becomes a dominant part of the resonant system as the cabling 9 gets longer. Similarly, the shielding of the cable is affected by electromagnetic interference, These effects reduce sensitivity and increase noise. However, the differential signaling reduces the effect of the capacitance of the cabling 9 as the shield is no longer a signal return path. Similarly, the signals are less affected by electromagnetic interference. Thus, the differential signaling improves the sensitivity and/or allows operation at increased oscillation frequencies. Similarly, the differential signaling improves the signal-to-noise ratio. Useful ranges of the length of the cabling 9 for the sensor system 1 may be from very short to very long, of the order of tens of meters. The differential signaling provides particular advantage where the length of the cabling is of the order of 4 m or more.

The probe 8 may be a capacitive or inductive element, as appropriate to the system and electrical properties to be sensed. The probe 8 generates an electromagnetic field in a sensing region, the electromagnetic filed oscillating with the oscillation of the marginal oscillator 2.

The probe 8 is used to sense electromagnetic properties of the contents of a pipe 10 formed of insulating material. The probe 8 comprises a pair of conductive rings 11 arranged around the pipe 10 outside the walls 13 of the pipe 10. The conductive rings 11 are disposed at positions spaced apart along the pipe 10. The conductive rings 11 form electrodes that capacitively couple through the walls 13 of the pipe 10 with the fluid inside and hence, by virtue of the fluid coupling properties, to each other. Accordingly, the probe 8 is a capacitive probe that forms the sensing region between the conductive rings 11 so that the sensing region extends across the interior of the pipe 10. This form of the probe 8 allows the contents of the pipe 10 to be sensed with a construction that is straightforward to implement without physically disrupting flow of the contents. The conductive rings 11 may be retro-fitted to an existing pipe 10 or may integrally formed with the pipe 10 to form a section that is fitted with other pipes. In either case, the pipe 10 will be connected other pipes by flanges 12, the construction and arrangement of which is variable and not known in advance. The geometry of the conductive rings 11, the pipe 10 and the frequency of operation can be adjusted to provide the best sensitivity over the desired range of the characteristic being sensed.

Many other forms of the probe 8 could be used to provide a capacitive probe. In the case of sensing the contents of a pipe, the probe 8 could take other forms such as plates extending only partway around the pipe, although the capacitive rings 11 have the advantage of providing an extensive sensing region with a simple construction. When used to sense other systems, the probe 8 could have an entirely different construction, ranging for example from a simple pair of planar plates to more complicated structures.

As an alternative, the probe 8 could be an inductive probe such as a cylindrical coil wrapped around the pipe that forms a sensing region that extends from inside the coil 15 to a region around the ends of the coil 15. More generally, the probe could be any form of antennae that generates an RF EM field inside the sample holder.

Many other forms of the probe 8 could be used to provide an inductive probe, for example a coil having other non-cylindrical shapes or a planar coil.

In use, the non-linear drive circuit 4 is operated to drive oscillation of the tank circuit 3 and the detection circuit 5 is operated to detect characteristics of the oscillation of the tank circuit 3 that are dependent on the electromagnetic properties of the contents of the sensing region, as described further below, and derives signals representing those characteristics.

The arrangement of the non-linear drive circuit 4 will now be described.

The non-linear drive circuit 4 provides differential signaling in that it supplies a differential signal pair of complementary signals on lines 20 across the tank circuit 3. The complementary signals are each formed with respect to a common ground, but in anti-phase with each other, although they may have unbalanced amplitudes as described further below. Thus, the overall signal appearing across the tank circuit 3 is the difference between the complementary signals and is independent of the ground which provides various advantages to the sensor system 1.

The non-linear drive circuit 4 has the following arrangement that sustains the oscillation on the basis of one of the complementary signals supplied back to the non-linear drive circuit 4 on line 21. In this example, the marginal oscillator 2 is a Robinson marginal oscillator including a separate gain stage 22 and limiter stage 23, the limiter stage 23 driving a current source stage 24. Although it is not essential for the marginal oscillator 2 to be a Robinson marginal oscillator, this provides the advantages of a Robinson marginal oscillator that are known in themselves.

The gain stage 22 is supplied with a single one of the complementary signals supplied back on line 21 and amplifies that signal to provide a differential pair of amplified outputs. In this example, the gain stage 22 is formed by an operational amplifier 25 that amplifies the complementary signal supplied back from the tank circuit 3. That complementary signal from the tank circuit 3 is DC coupled to one of the inputs of the operational amplifier 25, the other input of the operational amplifier 25 being grounded.

The limiter stage 23 is supplied with the differential pair of amplified outputs from the gain stage 22 and limits those outputs to provide a differential pair of limited outputs on lines 26. In this example, the limiter stage 23 is formed by a pair of limiters 27 that each limit the amplitude of one of the differential pair of amplified outputs.

The current source stage 24 is driven by the differential pair of limited outputs from the limiter stage 23 and converts them into the differential signal pair of complementary signals that are supplied across the tank circuit 3. The current source stage 24 converts the voltage signals into currents and has a differential output. The current source stage 24 comprises a pair of current sources 28 each receiving one of the limited outputs on lines 26. Each current source 28 may be formed by a passive element, for example a resistor or a capacitor that converts the voltage of the input into a current. Alternatively, each current source 28 may be an active component such as a semiconductor device or an amplifier. The feedback of the complementary signal from the tank circuit 3 to the gain stage 22 is positive and in combination with the action of the limiter stage 23 builds up and sustains the oscillation of the tank circuit 3 at the natural frequency of the tank circuit 3.

The current sources 28 may be identical so that the complementary signals supplied across the tank circuit 3 are of equal amplitude. However, advantageously the current sources 28 may be unbalanced, that is have different voltage-to-current gains. As a result, the complementary signals supplied across the tank circuit 3 have unbalanced amplitudes. By creating such a difference in the amplitudes of the complementary signals to ensure that the inverting output is more dominant than the non-inverting output, reliable starting of the marginal oscillator 2. The unbalanced nature of the complementary signals provides an anti-hysteresis effect.

In the above example, a differential pair of signals is supplied through the non-linear drive circuit from the gain stage 22 onwards. However, in general the gain stage 22 or both the gain stage 22 and the limiter stage 23 could output single ended signals, provided that the output from the current source stage 24 is a differential pair of complementary signals.

In the above example, the non-linear drive circuit 4 is supplied with a single one of the complementary signals supplied back on line 21. As an alternative, the non-linear drive circuit 4 may be supplied with both the complementary signals supplied back to the non-linear drive circuit 4, on line 21 and additionally on line 29 which is shown in dotted outline. The non-linear drive circuit 4 then sustains the oscillation of the tank circuit 3 using the complementary signals differentially. In the case of the non-linear drive circuit 4 being formed by the gain stage 22 and the limiter stage 23 shown in FIG. 1, the complementary signals are DC coupled to the two inputs of the operational amplifier 25 of the gain stage 22, instead of one of the inputs of the operational amplifier 25 being grounded. This alternative may provide lower noise since the non-inverting and inverting inputs will cross at a faster rate, although start up may require an additional circuit.

The detection circuit 5 has the following arrangement for detecting characteristics of the oscillation of the tank circuit 3.

Firstly, the detection circuit 5 is arranged to detect the amplitude of the oscillation of the tank circuit 3 as follows.

This detection is performed differentially using the differential pair of complementary signals. Alternatively, the detection could be performed in a similar manner but using one of the complementary signals as a single-ended signal. That would simplify the detection circuit 5, but the differential detection improves accuracy and reduces the signal-to-noise ratio.

The detection circuit 5 includes a pair of rectifiers 31 each supplied with one of the complementary signals. The rectifiers 31 each perform half-wave rectification, but selecting halves of the complementary signals of opposite polarities, so that the outputs of the pair of rectifiers form a differential pair of rectified signals. The rectifiers 31 may be implemented in a conventional manner by diode chains. As an alternative, the rectifiers 31 could perform full-wave rectification.

The detection circuit 5 further includes a pair of low-pass filters 32 each supplied with one of the rectified signals output by the pair of rectifiers 31. Each low-pass filter 32 simply outputs the average level of the respective rectified signal. The low-pass filters 32 may have any construction to achieve this, including a being very simple smoothing circuit formed by a series resistor and parallel capacitor. Due to the rectification, each output is proportional to the amplitude of the corresponding one of the complementary signals.

The detection circuit 5 further includes a differential amplifier 33 supplied with the outputs of the pair of low-pass filters 32. The differential amplifier 33 therefore outputs the differential amplitude of outputs, which is proportional to the differential amplitude of the differential pair of complementary signals across the tank circuit 3. Accordingly, differential amplifier 33 outputs a signal representing the amplitude of the oscillation of the tank circuit 3.

The above circuitry for detecting the amplitude of the oscillation of the tank circuit 3 is simple and straightforward to implement, although in general other arrangements could be implemented.

Secondly, the detection circuit 5 includes a frequency counter 30 that is connected to one of the signal lines 26 between the gain stage 22 and the amplifier stage 23 of the non-linear drive circuit 4 (although in general it could be supplied with an oscillating signal from any other point in the marginal oscillator 2). Thus, the frequency counter 30 serves as a detector that detects the frequency of the oscillation of the tank circuit 3. The frequency counter 30 outputs a signal representing that frequency of oscillation.

Although the detection circuit 5 in this example detects the amplitude and frequency of the oscillation of the tank circuit 3, in general any other characteristic of the oscillation could be additionally or alternatively detected, for example the Q factor.

The sensor system 1 includes a fault detection unit 34 that is supplied with the signal output from the detection circuit 4 that is representing the frequency of the oscillation of the tank circuit 3. The fault detection unit 34 monitors that signal and generates a fault signal when the frequency is indicative of a fault state due to being outside a predetermined band of normal operation. This is possible because of the differential nature of the signals across the tank circuit 3. That is, in the case that the probe 8 is an inductive probe, then the frequency being unusually high prompts a fault signal indicating shorting of the probe 8 (closed circuit case) and the frequency becoming zero prompts a fault signal indicating removal of the probe 8 (open circuit case) Similarly, in the case that the probe 8 is a capacitive probe, then the frequency being unusually high prompts a fault signal indicating removal or shorting of the probe 8.

All the signals output from the detection circuit 4 are supplied to a signal analysis unit 35 that may analyze those signals. The signal analysis unit 35 may be implemented by any suitable data processing system, for example a computer apparatus including processor executing an appropriate program or dedicated hardware. The analysis performed by the signal analysis unit 35 depends on the system and electromagnetic properties that are being sensed. Merely by way of example, the signal analysis unit 35 may analyze the signal representing the amplitude of the oscillation of the tank circuit 3 to generate a signal representing the conductivity of the contents of the sensing region.

The differential signaling used in the sensor system 1 provides an advantage arises that the ground is electrically isolated from the rest of the system. This reduces the effects of uncontrolled ground paths associated with the probe which may otherwise introduce error in the sensing by affecting the detected characteristic in an unpredictable manner. For example in the probe 8 of FIG. 2, the impact of the pair of flanges 12 on the detected signal is reduced significantly compared to use of a single-ended signal. By reducing such effects, the accuracy of the sensing may be improved and/or the screening requirements of the probe may be reduced resulting in easier implementation of the probe in respect of the system being sensed.

Three non-limitative examples of applications of the sensor system 1 are as follows.

The first application for the sensor system 1 is to sense a sample obtained during hydrocarbon exploration or production. The sample may include water and/or hydrocarbons in unknown quantities. The sample may be the contents of a pipe, in which case the probe 8 may be a capacitive probe, for example that shown in FIG. 2.

Such a sample including water and hydrocarbons can co-exist in a water-continuous phase (i.e. oil suspended in water) or an oil-continuous phase (i.e. water suspended in oil), or switch between these two phases in some random and unpredictable fashion. Such a sample is conductive in the water-continuous phase but not in the oil-continuous phase. This effect may be used to determine the state of the fluid at any instant, so that the appropriate measurement technique may be applied and other measurements can be appropriately calibrated, as follows.

In this application the signal analysis unit 35 analyses the signal representing the amplitude of the oscillation of the tank circuit 3 to generate a signal representing the conductivity of the contents of the sensing region. In the case that the conductivity is zero (or below a low threshold), then the signal analysis unit 35 outputs a signal indicating that the contents of the pipe are in the oil-continuous phase. Otherwise, the signal analysis unit 35 outputs a signal indicating that the contents of the pipe are in the water-continuous phase, and may output the signal representing the conductivity.

In the latter case, further analysis may be performed when the water cut, i.e. the proportion of water in the sample, is also known. The water cut may be known for example from another measurement taken by the sensor system 1 or another sensor system. In this case, the signal analysis unit 35 may also derive a signal representing the salinity of the sample. This assumes that the conductivity of the sample has no contribution from the hydrocarbons and so is derived solely from the water. It also takes into account the known relationship between the conductivity of the water and its salinity.

Figure 4:
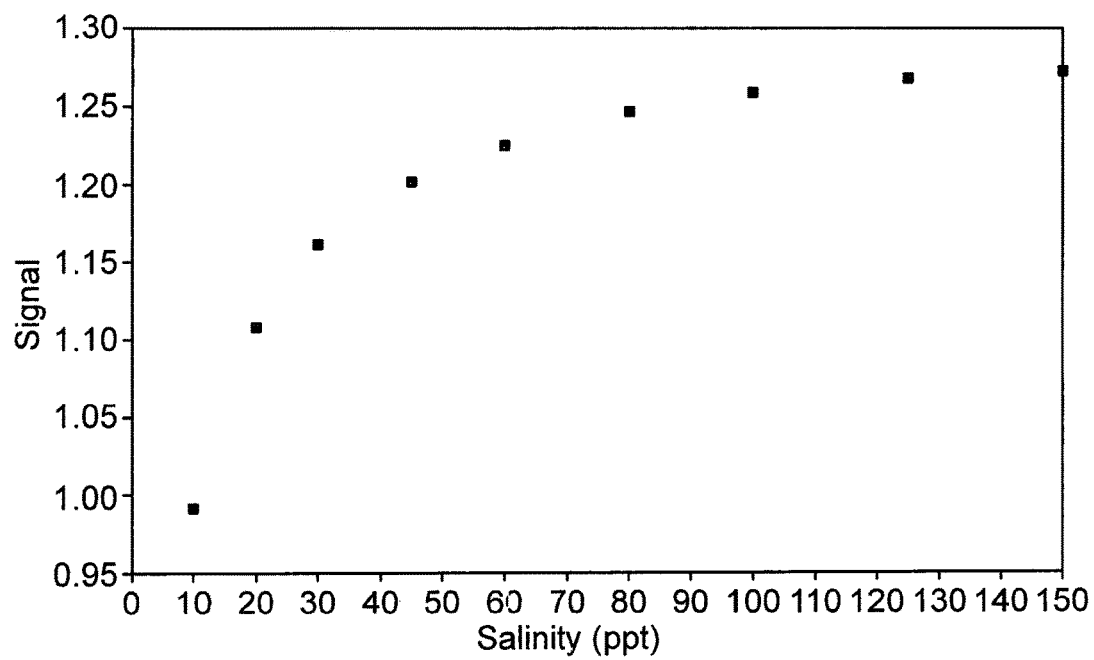
FIG. 4 is a graph of the amplitude of oscillation against salinity of the contents of the pipe detected by the sensor system of FIG. 1 using the probe of FIG. 2.

In this application, the sensor system 1 provides a stable way of sensing a conductivity signal over a wide range of salinities By way of example, FIG. 4 shows the response of the sensor system 1 for a range of samples of pure water of different salinity, being a graph of the signal representing the amplitude of the oscillation of the tank circuit against salinity. As can be seen, the sensor system 1 has a logarithmic response to the salinity and therefore has a wide dynamic range. The geometrical and electrical parameters of the sensor system 1 can be tuned to provide the best sensitivity for the range of interest. Generally the sensor system 1 provides a salinity/conductivity range of 1.5 orders of magnitude.

The second application for the sensor system 1 is to sense a fluid sample containing a mixture of two or more components to obtain a measure of the proportion of one or more of the components. By way of example, the components may be without limitation any selected from the following list: water, hydrocarbons, fuels (of any type including biofuels), sugars, alcohols, drilling fluids, lubricants. The mixture may include components which are different members of that list, or different types of the same member of that list. Some examples of particular mixtures include be without limitation: biofuel and petrol; biofuel and diesel; hydrocarbon and water (which might or might not be a sample obtained during hydrocarbon exploration or production which is the first application); ice and water; alcohol and water; alcohol and sugar; or sugar and water.

Figure 2:
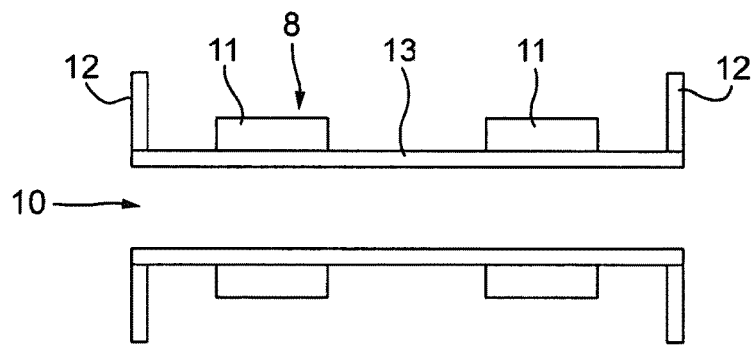
FIG. 2 is a cross-sectional view of a probe of the sensor system providing a sensing region in a pipe.
Figure 3:
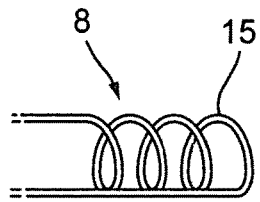
FIG. 3 is a schematic side view of a probe that is a cylindrical coil.

In this application, the sample may be the contents of a pipe, in which case the probe 8 may be a capacitive probe, for example that shown in FIG. 2.

In this application, the signal analysis unit 35 analyses the signal representing the amplitude of the oscillation of the tank circuit 3 to generate a signal representing the conductivity of the contents of the sensing region. On the basis of the conductivity, the signal analysis unit 35 may further generate a signal representing the proportion of a component of the mixture, taking into account the relative conductivities of the components. The signal analysis unit 35 may take into account measurements of other parameters taken by the sensor system 1 or another sensor system.

In either the second or third applications, the signal analysis unit 35 may perform analysis to derive a signal representing the conductivity taking into account the geometry and known electromagnetic properties of the probe 8. For example, this may be done in the case of that the probe 8 is the capacitive probe shown in FIG. 2, as follows.

The following geometrical parameters of the probe 8 are shown in FIG. 2 and may be tuned to change the operation of the sensor system 1:

$P_w$=thickness of the walls 13 of the pipe 10 (thinner wall thickness implies higher salinities can be measured);

$D_c$=length of the conductive rings 11 (greater length implies higher salinities can be measured);

$D_g$=gap between conductive rings 11 (greater length implies higher salinities can be measured);

$P_{id}$=diameter of the pipe 10 (smaller diameter implies higher salinities can be measured); and F=frequency of oscillation (higher frequency implies higher salinities can be measured).

Taking into account the above parameters, the signal analysis unit 35 can determine the conductivity of the contents of the sensing region using the following equations:

$\sigma_f$=Fluid conductivity($Sm^{-1}$)

$\sigma(S)=\sigma_f \cdot \pi \cdot (P_{id}/2)^2$ $C_s=(P_{id}+P_w)\cdot \pi \cdot D_c \cdot \varepsilon_w/2P_2$ $\omega=2\pi f$ $Q=\sigma/\omega \cdot C_s$ $R_p=(Q^2+1)/\sigma$ $Cp=(C_s \cdot Q^2)/(1+Q^2)$ Rp is the value of interest, the optimum slope being obtained when the value of Rp is the same as the other loses in the circuit. As Rp changes quickly, a variation of circuit losses between 2 kΩ-10 kΩ does not make that much difference.

The third application for the sensor system 1 is to detect nuclear magnetic resonance (NMR). For example, the sensor system 1 may be used in the apparatus and method described in British Patent Appl. No. 1408862.9 to detect the amount of one or more types of nuclei. In that case, the probe 8 is formed by an RF coil coiled around a sample holder as described in British Patent Appl. No. 1408862.9.

When producing measurements from NMR, a very sensitive set of detection electronics is needed. NMR detection systems generally involve the use of amplifiers with large gains (typically gains of the order of 1000 or more). As the signal is so weak, any noise in the system can become dominant, especially in the case of continuous wave NMR mains noise, where the sweep frequency used will be similar. This is particularly important in the weaker signals from nuclei with lower Hz/Tesla values.

If a single ended sensor system is used, ground noise is inevitably picked up and amplified. The differential signaling employed in the sensor system 1 eliminates these noise sources thereby improving performance and sensitivity.

The invention claimed is:

1. A system, comprising:
 a sensor arrangement including:
  a marginal oscillator and a detection circuit, wherein the marginal oscillator includes:
   a tank circuit including inductive and capacitive elements that include an inductive or capacitive probe arranged to generate an electromagnetic field in a sensing region; and
   a non-linear drive circuit arranged to drive oscillation of the tank circuit by supplying a differential signal pair of complementary signals across the tank circuit, the non-linear drive circuit being arranged to sustain the oscillation on the basis of at least one of the differential signal pair of complementary signals supplied back to the non-linear drive circuit, wherein the detection circuit is arranged to detect at least one characteristic of the oscillation of the tank circuit that is dependent on the electromagnetic properties of the contents of the sensing region and to derive a signal representing the at least one characteristic.

2. The system according to claim 1, wherein said at least one characteristic of the oscillation of the tank circuit includes the amplitude of the oscillation of the tank circuit.

3. The system according to claim 2, wherein the detection circuit is arranged to differentially detect the amplitude of the oscillation of the tank circuit.

4. The system according to claim 2, wherein further comprising a signal analysis unit arranged to analyze the derived signal representing the amplitude of the oscillation of the tank circuit and to generate therefrom a signal representing the conductivity of the contents of the sensing region.

5. The system according to claim 1, wherein said at least one characteristic of the oscillation of the tank circuit includes the frequency of the oscillation of the tank circuit.

6. The system according to claim 5, further comprising a fault detection unit arranged to analyze the derived signal representing the frequency of the oscillation of the tank circuit and to generate a fault signal when the frequency is outside a predetermined band.

7. The system according to claim 1, wherein the probe is a capacitive probe.

8. The system according to claim 7, wherein the probe comprises a pair of conductive rings arranged around a pipe formed of insulating material at positions spaced apart along the pipe, thereby forming the sensing region therebetween.

9. The system according to claim 1, wherein the probe is an inductive probe.

10. The system according to claim 1, wherein the probe is connected to the remainder of the tank circuit by cabling.

11. The system according to claim 1, wherein the differential signal pair of complementary signals have unbalanced amplitudes.

12. The system according to claim 1, wherein the marginal oscillator is a Robinson marginal oscillator.

13. The system according to claim 1, wherein the non-linear drive circuit comprises:
a gain stage arranged to amplify the at least one of the differential signal pair of complementary signals supplied back to the non-linear drive circuit and provide a differential pair of amplified outputs;
a limiter stage arranged to limit the differential pair of amplified outputs and provide a differential pair of limited outputs; and
a current source stage driven by the differential pair of limited outputs and arranged to provide the differential signal pair of complementary signals.

14. The system according to claim 1, wherein the non-linear drive circuit is arranged to sustain the oscillation on the basis of a single one of the differential signal pair of complementary signals supplied back to the non-linear drive circuit.

15. The system according to claim 1, wherein the non-linear drive circuit is arranged to sustain the oscillation on the basis of both the differential signal pair of complementary signals supplied differentially back to the non-linear drive circuit.

16. A method comprising:
utilizing a marginal oscillator including: a tank circuit having inductive and capacitive elements that include an inductive or capacitive probe arranged for:
generating an electromagnetic field in a sensing region;
wherein the marginal oscillator further includes a non-linear drive circuit arranged to drive oscillation of the tank circuit by:
supplying a differential signal pair of complementary signals across the tank circuit, wherein the non-linear drive circuit is arranged for sustaining the oscillation on the basis of at least one of the differential signal pair of complementary signals supplied back to the non-linear drive circuit,
wherein the marginal oscillator is operated for:
providing oscillation of the tank circuit, and
detecting at least one characteristic of the oscillation of the tank circuit that is dependent on the electromagnetic properties of the contents of the sensing region.

* * * * *